US012765483B2

(12) United States Patent
Roosenboom-Kooijmans

(10) Patent No.: US 12,765,483 B2
(45) Date of Patent: Oct. 20, 2026

(54) LETTUCE VARIETY 41-CR2360 RZ

(71) Applicant: RIJK ZWAAN ZAADTEELT EN ZAADHANDEL B.V., De Lier (NL)

(72) Inventor: Maria Helena Roosenboom-Kooijmans, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 330 days.

(21) Appl. No.: 18/507,811

(22) Filed: Nov. 13, 2023

(65) Prior Publication Data

US 2024/0155991 A1 May 16, 2024

Related U.S. Application Data

(60) Provisional application No. 63/383,524, filed on Nov. 14, 2022.

(51) Int. Cl.
*A01H 6/14* (2018.01)
*A01H 5/12* (2018.01)

(52) U.S. Cl.
CPC ............. *A01H 6/1472* (2018.05); *A01H 5/12* (2013.01)

(58) Field of Classification Search
None
See application file for complete search history.

(56) References Cited

U.S. PATENT DOCUMENTS

| | | | |
|---|---|---|---|
| 7,371,930 | B1 | 5/2008 | Knerr |
| 8,809,631 | B2 | 8/2014 | van Dun |
| 9,161,510 | B2 | 10/2015 | Ammerlaan |
| 9,326,479 | B2 | 5/2016 | Roosenboom-Kooijmans |
| 9,370,163 | B2 | 6/2016 | Moor |
| 9,554,550 | B2 | 1/2017 | Roosenboom-Kooijmans |
| 10,321,651 | B2 | 6/2019 | Roosenboom-Kooijmans et al. |
| 10,426,117 | B2 | 10/2019 | Luijten |
| 10,492,407 | B2 | 12/2019 | Tomas Garcia et al. |
| 2013/0019336 | A1 | 1/2013 | Moor |
| 2017/0094930 | A1 | 4/2017 | Smits |
| 2017/0156283 | A1 | 6/2017 | Ammerlaan |
| 2019/0037790 | A1 | 2/2019 | Morice |
| 2019/0098856 | A1 | 4/2019 | Kunzemann |
| 2019/0141932 | A1 | 5/2019 | Roosenboom-Kooijmans et al. |
| 2019/0141933 | A1 | 5/2019 | Roosenboom-Kooijmans et al. |
| 2019/0150387 | A1 | 5/2019 | Roca |
| 2019/0191653 | A1 | 6/2019 | Roosenboom-Kooijmans et al. |
| 2019/0364773 | A1 | 12/2019 | de Jong |
| 2020/0146237 | A1 | 5/2020 | Moor |
| 2020/0214239 | A1* | 7/2020 | Munoz Munoz ........ A01H 5/12 |

OTHER PUBLICATIONS

Bairu et al. (2011) Plant Growth Regul 63:147-73.*
Haun et al. (2011) Plant Physiol. 155:645-55.*
Großkinsky et al. (2015) J. Exp. Bot. 66:5429-40.*
UPOV (2017) Explanatory Notes on Essentially Derived Varieties Under the 1991 Act of the UPOV Convention.*
USDA (2023) Applying for a Plant Variety Certificate of Protection.*
IBEB press release New race of Bremia lactucae 81:27 identified and nominated, May 2010; Plantum NL, Postbus 462, 2800 Al Gouda.
Michelmore R. & Ochoa. O. Breeding Crisphead Lettuce. In: California Lettuce Research Board, Annual Report 2005-2006, 2006, Salinas, California, pp. 55-68.
Schettini, T.M., Legg, E.J., Michelmore, R.W., 1991. Insensitivity to metalaxyl in California populations of Bremia lactucae and resistance of California lettuce cultivars to Downy Mildew, Disease Control and Pest Management, pp. 64-70.
Van Ettekoven, K. et al., Identification and denomination of 'new' races of Bremia lactucae, In: Lebeda, A. and Kristkova, E (eds.), Eucarpia Leafy Vegetables, 1999.
Van der Arend et al. Identification and denomination of "new" races of Bremia lactucae in Europe by IBEB until 2002. In: Van Hintum, Th et al. (eds.), Eucarpia Leafy Vegetables.
Cortazar RZ (41-233) Rijk Zwaan AU (Oct. 22, 2019).
Lettuce: Lettuce Resources, Rijk Zwaan AU 2019 (Oct. 22, 2019).
Lalique RZ 44-17—Rijk Zwaan USA and Canada (2018).
UPOV Document TG/244/1 Wild Rocket UPOV Code: Di Plo_ Ten Diplotaxis tenuifolia (L.) DC. Date: Apr. 9, 2008.
Beiquan Mou, Review Article: Mutations in Lettuce Improvement, Hindawi Publishing Corporation, International Journal of Plant Genomics, Nov. 16, 2011) vol. 2011, Article ID 723518, 7 pages.
Ex parte Berg, Appeal 2022-003691, Decision on Appeal issued Oct. 14, 2022 in U.S. Appl. No. 13/336,477.
Ex parte Berg, Appeal 2024-002212, Decision on Appeal issued Oct. 21, 2024 in U.S. Appl. No. 18/054,639.
Ex parte C, 27 USPQ2d 1492 (BPAI 1992) 1992 WL 515817.
*Enzo Biochem, Inc.* v. *Gen-Probe Inc.*, 323 F.3d 956 (Fed. Cir. 2002).
Ex parte Kikuchi, Appeal No. 2006-3084, Decision on Appeal issued Mar. 16, 2007, in U.S. Appl. No. 10/673,860.
Ex parte Winner, Appeal 2020-000054, Decision on Appeal issued Apr. 16, 2020 in U.S. Appl. No. 14/931,601.

* cited by examiner

*Primary Examiner* — Russell T Boggs
(74) *Attorney, Agent, or Firm* — Duane Morris LLP; Thomas J. Kowalski

(57) ABSTRACT

The present invention relates to a *Lactuca sativa* seed designated 41-CR2360 RZ. The present invention also relates to a *Lactuca sativa* plant produced by growing the 41-CR2360 RZ seed. The invention further relates to methods for producing the lettuce cultivar, represented by lettuce variety 41-CR2360 RZ.

26 Claims, 4 Drawing Sheets

1. 2. 3. 4. 5. 6.

| Year | Description | Location |
|---|---|---|
| 0 | Final F1 cross in glasshouse | Fijnaart, The Netherlands |
| 1 | F1 plant grown for F2 seed production in glasshouse | Fijnaart, The Netherlands |
| 1-2 | F2 plant selected in open field, followed by F3 seed production | Fijnaart, The Netherlands |
| 2 | F3 plant selected in open field, followed by F4 seed production | Fijnaart, The Netherlands |
| 4-5 | F4 plant selected in open field, followed by F5 seed production | Murcia, Spain |
| 5-6 | F5 plant selected in open field, followed by F6 seed production | Murcia, Spain |
| 7 | F6 line established uniform, multiplied in plastic tunnel seed lot 21R.1360 | Daylesford, Australia |

FIG. 2

FIG. 3A

| | |
|---|---|
| **SEED** | |
| Seed Color | White |
| **PLANT** | |
| Plant: Plant Diameter (Plant Head Diameter) | Small |
| Plant: Degree of Overlapping of Upper Part of Leaves | medium |
| **LEAF** | |
| Leaf: Leaf Attitude | Semi-Erect |
| Leaf: Number of Divisions | Absent or very few |
| Leaf: Shape | Medium elliptic |
| Leaf: Shape of Apex | Rounded |
| Leaf: Longitudinal Section | Flat |
| Leaf: Width of Lobes | Medium to broad |
| Leaf: Anthocyanin Coloration | Absent or very weak |
| Leaf: Color | Greyish green |
| Leaf: Intensity of Green Color | Medium |
| Leaf: Glossiness of Upper Side | Very weak to weak |
| Leaf Thickness | Thick |
| Leaf: Blistering | Weak |
| Leaf: Size of Blisters | Very small to small |
| Leaf: Undulation of Margin | Absent or very weak |
| Leaf: Venation | Not Flabellate |
| **HEAD** | |
| Head: Size | Small |
| Head: Shape in Longitudinal Section | Narrow elliptic |
| Head: Density | Dense |
| **HARVEST** | |
| Time of Harvest Maturity | Medium to late |
| **BOLTING** | |
| Bolting: Time of Beginning of Bolting | Very late |
| Auxilliary Sprouting | Absent or weak |
| Bolting: Bolting Stem: Fasciation | Very weak to weak |
| **PLANT TYPE** | |
| Plant Type | |

FIG. 3B

| | |
|---|---|
| **COTYLEDON TO FOURTH LEAF STAGE** | |
| Shape of Cotyledons | Intermediate |
| Shape of Fourth Leaf | Elongated |
| **PLANT** | |
| Plant Diameter (Plant Head Diameter) | 10 cm |
| Plant Spread of Frame Leaves | 26 cm |
| Plant Number of Leaves | - |
| **LEAF** | |
| Leaf: Number of Divisions | 1 |
| **BUTT** | |
| Butt: Shape | Rounded |
| Butt: Midrib | Moderately raised |
| **HARVEST MATURITY** | |
| Time of harvest Maturity | 107 Days |

LETTUCE VARIETY 41-CR2360 RZ

RELATED APPLICATIONS AND INCORPORATION BY REFERENCE

This application claims benefit of and priority to U.S. provisional patent application Ser. No. 63/383,524, filed Nov. 14, 2022.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new lettuce (*Lactuca sativa*) variety designated 41-CR2360 RZ. Lettuce variety 41-CR2360 RZ exhibits a combination of traits including resistance to downy mildew (*Bremia lactucae*) races B1:29EU to B1:30EU, B1:32EU, BL:33EU and Bl: 1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head.

BACKGROUND OF THE INVENTION

All cultivated forms of lettuce belong to the highly polymorphic species, *Lactuca sativa*, which is grown for its edible head and leaves. As a crop, lettuces are grown commercially wherever environmental conditions permit the production of an economically viable yield.

*Lactuca sativa* is in the Cichoreae tribe of the Asteraceae (Compositae) family. Lettuce is related to chicory, sunflower, aster, scorzonera, dandelion, artichoke and *chrysanthemum. Sativa* is one of about 300 species in the genus *Lactuca*.

Lettuce cultivars are susceptible to a number of pests and diseases such as downy mildew (*Bremia lactucae*). Every year this disease leads to millions of dollars of lost lettuce crop throughout the world. Downy mildew (*Bremia lactucae*) is highly destructive on lettuce grown at relatively low temperature and high humidity. Downy mildew is caused by a fungus, *Bremia lactucae*, which can be one of the following strains: Bl:16EU, Bl:17EU, Bl:18EU, B1:20EU, B1:21EU, B1:22EU, B1:23EU, B1:24EU, B1:25EU, B1:26EU, B1:27EU, B1:29EU, B1:30EU, B1:31EU, B1:32EU, B1:33EU, B1:34EU, B1:35EU, B1:36EU, B1:37EU, B1:39EU, B1:40EU (Van Ettekoven, K. et al., "Identification and denomination of 'new' races of *Bremia lactucae*," In: Lebeda, A. and Kristkova, E. (eds.), Eucarpia Leafy Vegetables, 1999, Palacky University, Olomouc, Czech Republic, pp. 171-175; Van der Arend et al. "Identification and denomination of "new" races of *Bremia lactucae* in Europe by IBEB until 2002" In: Van Hintum, Th et al. (eds.), Eucarpia Leafy Vegetables Conference 2003, Centre for Genetic Resources, Wageningen, The Netherlands, p. 151; Plantum NL (Dutch association for breeding, tissue culture, production and trade of seeds and young plants), Van der Arend et al. "Identification and denomination of "new" races of *Bremia lactucae* in Europe by IBEB until 2002." In: Van Hintum, Th et al. (eds.), Eucarpia Leafy Vegetables Conference 2003, Centre for Genetic Resources, Wageningen, The Netherlands, p. 151; Plantum NL; IBEB press release "New race of *Bremia lactucae* B1:27 identified and nominated", May 2010; Plantum NL, IBEB press release, "New races of *Bremia lactucae*, B1:29, B1:30 and B1:31 identified and nominated", August 2013; Plantum NL, IBEB press release, "A new race of *Bremia lactucae*, B1:32 identified and nominated in Europe", May 2015); Plantum NL, IBEB-EU press release, "A new race of *Bremia lactucae*, B1:33EU identified and denominated in Europe", May 2017; Plantum NL, IBEB-EU press release, "Two new races of *Bremia lactucae*, B1:34EU and B1:35EU identified and nominated in Europe", July 2018; Plantum NL, IBEB-EU press release, "A new race of *Bremia lactucae*, B1:36EU identified and denominated in Europe", July 2019; Plantum NL, IBEB EU press release, "A new race of *Bremia* lactucae, B1:37EU identified and denominated in Europe, June 2021; IBEB-EU press release, "Denomination of New Official Downy Mildew Races in Lettuce", July 2023, europeanseed.com), Bl:1US, Bl:2US, Bl:3US, Bl:4US, Bl:5US, Bl:6US, Bl:7US, Bl:8US, Bl:9US (Schettini, T. M., Legg, E. J., Michelmore, R. W., 1991. Insensitivity to metalaxyl in California populations of *Bremia lactucae* and resistance of California lettuce cultivars to downy mildew. Phytopathology 81(1). p. 64-70; Michelmore R. & Ochoa. O. "Breeding Crisphead Lettuce, In: California Lettuce Research Board, Annual Report 2005-2006, 2006, Salinas, California, pp. 55-68; *bremia*.ucdavis.edu).

Downy mildew causes pale, angular, yellow areas bounded by veins on the upper leaf surfaces. Sporulation occurs on the opposite surface of the leaves. The lesions eventually turn brown, and they can enlarge and coalesce. These symptoms typically occur first on the lower leaves of the lettuce, but under ideal conditions can move into the upper leaves of the head. When the fungus progresses to this degree, the head cannot be harvested. Less severe damage requires the removal of more leaves than usual, especially when the lettuce reaches its final destination.

Of the various species of aphids that feed on lettuce, the currant-lettuce aphid (*Nasonovia ribisnigri*) is the most destructive species because it feeds both on the leaves of the lettuce as well as the heart of the lettuce, making it difficult to control with conventional insecticides. The lettuce aphid feeds by sucking sap from the lettuce leaves. Although direct damage to the lettuce can be limited, its infestation has serious consequences because the presence of aphids makes lettuce unacceptable to consumers.

Lettuce root aphids (*Pemphigus bursarius*) form clustered colonies on lettuce roots, covering them with a white powdery wax. Feeding on the roots cause the plants to wilt during the day. Individually affected rootlets turn brown and die. The developing heads remain soft, can fail to develop, and yields thus become reduced. Prolonged periods of infestation can cause the collapse and death of the plant.

Crunchy lettuce is a new type of lettuce which has the thick inner and outer leaves that provide a crisp and crunchy bite, and it has the leaf and oval head shape of Cos lettuce. Crunchy lettuce is particularly suitable for mechanical harvesting of whole heads or single leaves. It should provide an attractive product at harvestable stage which is accepted by consumers and/or the processing industry.

There are certain constraints that make lettuce varieties more fit or less fit for mechanical harvesting.

One constraint is caused by the use of mechanically-driven horizontal knives that easily damage the hollow main veins of leaves and cut halfway through the prostrate, round-shaped, lower outer leaves, which results in wide cut surfaces.

Another constraint is the requirement for a leaf to have a good shelf life. This means that the leaves should get through the washing and drying process in the factory without bruising or breaking. The leaves should be sufficiently thick and tough to avoid wilting.

The oval shape of the leaves and the very thick main veins of crunchy lettuce make it particularly suitable for mechanical harvesting.

For the purpose of whole head and heart production, it is important that the leaves are wide enough to overlap and maintain head integrity. Short core internodes and petioles give a closed base. A longer core internode can be compensated by a more erect leaf attitude, that causes the base to be closed. The closed base and overlapping head leaves reduce the product surface, resulting in less wilting and a longer shelf life. This is desired by traders, retailers, and consumers.

Citation or identification of any document in this application is not an admission that such document is available as prior art to the present invention.

SUMMARY OF THE INVENTION

Given the need expressed by relevant stakeholders for a lettuce variety which shows a combination of traits including resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head, the present invention addresses this need by providing a new type of lettuce (*Lactuca sativa*) variety, designated 41-CR2360 RZ.

The present invention provides a new lettuce (*Lactuca sativa*) variety designated 41-CR2360 RZ. This new lettuce variety exhibits a combination of traits including resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head.

Representative seed comprising, or providing, and having the heritable genetic information for this combination of traits (including resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head), have been deposited with the National Collections of Industrial, Marine and Food Bacteria (NCIMB) in Wellheads Place, Dyce, Aberdeen AB21 7 GB, UK and have been assigned NCEVIB Accession No. 44249.

The present invention provides seed of a lettuce (*Lactuca sativa*) variety designated 41-CR2360 RZ. A sample of seeds of said lettuce variety, have been deposited with the National Collections of Industrial, Marine and Food Bacteria (NCIMB) in Wellheads Place, Dyce, Aberdeen AB21 7 GB, UK and have been assigned NCIMB Accession No. 44249.

In one embodiment, the invention provides a lettuce plant grown from the seed of lettuce (*Lactuca sativa*) variety 41-CR2360 RZ.

In another embodiment, the invention provides a lettuce plant designated 41-CR2360 RZ, which is a plant grown from seed having been deposited under NCIMB Accession No. 44249 or representative seed of which having been deposited under NCIMB Accession 44249. In one embodiment, the invention provides for a lettuce plant which can comprise genetic information for exhibiting the aforementioned combination of traits or resistances (including resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head) or for exhibiting all of the physiological and morphological characteristics of a plant of the invention, wherein the genetic information is as contained in a plant, a sample of seed of said variety having been deposited under NCIMB Accession No. 44249.

For example, a plant having all of the physiological and morphological characteristics of a plant of the invention can be a plant grown from deposited seed.

In one embodiment, the invention provides for a lettuce plant exhibiting for exhibiting the aforementioned combination of traits or resistances (including resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head) or exhibiting all the physiological and morphological characteristics of a plant of the invention, and having the genetic information for so exhibiting the combination of traits, wherein the genetic information is as contained in a plant, a sample of seed of said variety having been deposited under NCIMB Accession No. 44249.

In an embodiment of the present invention, there also is provided a lettuce plant or parts of a lettuce plant of the invention, which can include parts of a lettuce plant exhibiting the aforementioned combination of traits or resistances (including resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head) or exhibiting all the physiological and morphological characteristics of a plant of the invention, (e.g., a plant exhibiting all of the physiological and morphological characteristics of a plant of the invention can be a plant grown from deposited seed), or parts of a lettuce plant having any or all of the mentioned resistance(s) and/or a combination of traits including one or more or all morphological and physiological characteristics tabulated herein, including parts of lettuce variety 41-CR2360 RZ, wherein the plant parts are involved in sexual reproduction, which include, without limitation, microspores, pollen, ovaries, ovules, embryo sacs or egg cells and/or wherein the plant parts are suitable for vegetative reproduction, which include, without limitation, cuttings, roots, stems, cells or protoplasts and/or wherein the plant parts are tissue culture of regenerable cells in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems. The plants of the invention from which such parts can come from include those wherein a sample of seed of which having been deposited under NCIMB Accession No. 44249 or lettuce variety or cultivar designated 41-CR2360 RZ, as well as seed from such a plant, plant parts of such a plant (such as those mentioned herein) and plants from such seed and/or progeny of such a plant, advantageously progeny exhibiting such combination of such traits, each of which, is within the scope of the invention; and such combination of traits.

In a further embodiment there is a plant regenerated from the above-described plant parts or regenerated from the above-described tissue culture. Advantageously such a plant can have morphological and/or physiological characteristics of lettuce variety 41-CR2360 RZ and/or of a plant grown from seed, a sample of seed of which having been deposited under NCIMB Accession No. 44249—including without limitation such plants having all of the physiological and morphological characteristics of lettuce variety 41-CR2360 RZ and/or of a plant grown from seed, a sample of seed of which having been deposited under NCIMB Accession No. 44249.

Accordingly, in still a further embodiment, there is provided a lettuce plant having all of the physiological and morphological characteristics of lettuce variety 41-CR2360 RZ, a sample of seed of which having been deposited under NCEVIB Accession No. 44249. Such a plant can be grown from the seeds, regenerated from the above-described plant parts, or regenerated from the above-described tissue culture. A lettuce plant having any of the aforementioned resistance(s), and one or more morphological or physiological characteristics recited or tabulated herein, and a lettuce plant advantageously having all of the aforementioned resistances and the characteristics recited and tabulated herein, are preferred. Parts of such plants—such as those plant parts above-mentioned—are encompassed by the invention.

In a further aspect, the invention provides a method of vegetatively propagating a plant of lettuce variety 41-CR2360 RZ which can comprise (a) collecting tissue capable of being propagated from a plant of lettuce 41-CR2360 RZ, a sample of seed of said variety having been deposited under NCEVIB Accession No. 44249 and (b) cultivating the tissue to obtain proliferated shoots and rooting the proliferated shoots to obtain rooted plantlets. Optionally the invention further can comprise growing plants from the rooted plantlets. Plantlets and plants produced by these methods, are encompassed by the invention.

In one embodiment, there is provided a method for producing a progeny of lettuce cultivar 41-CR2360 RZ which can comprise crossing a plant designated 41-CR2360 RZ with itself or with another lettuce plant, harvesting the resultant seed, and growing said seed.

In a further embodiment, a progeny plant is provided which is produced by this method, wherein said progeny exhibits a combination of traits including resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head.

In another embodiment, a progeny plant is provided which is produced by the above method, wherein said progeny exhibits all the morphological and physiological characteristics of the lettuce variety designated 41-CR2360 RZ, a sample of seed of said variety having been deposited under NCEVIB Accession No. 44249.

In a further embodiment there is provided a progeny plant produced by sexual or vegetative reproduction, grown from seeds, regenerated from the above-described plant parts, or regenerated from the above-described tissue culture of the lettuce cultivar or a progeny plant thereof, a sample of seed of which having been deposited under NCIMB Accession No. 44249. The progeny can have any of the aforementioned resistance(s), and one or more morphological or physiological characteristics recited or tabulated herein, and a progeny plant advantageously having all of the aforementioned resistances and the characteristics recited and tabulated herein, are preferred.

Progeny of the lettuce variety 41-CR2360 RZ can be modified in one or more other characteristics, in which the modification is a result of, for example and without limitation, mutagenesis or transformation with a transgene.

In still another embodiment, the present invention provides progeny of lettuce cultivar 41-CR2360 RZ produced by sexual or vegetative reproduction, grown from seed, regenerated from the above-described plant parts, or regenerated from the above-described tissue culture of the lettuce cultivar or a progeny plant thereof.

The invention further relates to a method for producing a seed of a 41-CR2360 RZ-derived lettuce plant, which can comprise (a) crossing a plant of lettuce variety 41-CR2360 RZ, a sample of seed of which having been deposited under NCIMB Accession No. 44249, with a second lettuce plant, and (b) whereby seed of a 41-CR2360 RZ-derived lettuce plant forms. This method can further comprise (c) crossing a plant grown from 41-CR2360 RZ-derived lettuce seed with itself or with a second lettuce plant to yield additional 41-CR2360 RZ-derived lettuce seed, (d) growing the additional 41-CR2360 RZ-derived lettuce seed of step (c) to yield additional 41-CR2360 RZ-derived lettuce plants, and (e) repeating the crossing and growing of steps (c) and (d) for an additional 3-10 generations to generate further 41-CR2360 RZ-derived lettuce plants, and (f) whereby seed of a 41-CR2360 RZ-derived lettuce plant forms. A seed produced by this method and a plant grown from said seed also form part of the invention.

The invention also relates to a method of introducing at least one new trait into a plant of lettuce variety 41-CR2360 RZ, which can comprise: (a) crossing a plant of lettuce variety 41-CR2360 RZ, a sample of seed of which having been deposited under NCIMB Accession No. 44249, with a second lettuce plant that can comprise at least one new trait to produce progeny seed, (b) harvesting and planting the progeny seed to produce at least one progeny plant of a subsequent generation, wherein the progeny plant can comprise the at least one new trait, (c) crossing the progeny plant with a plant of lettuce variety 41-CR2360 RZ to produce backcross progeny seed, (d) harvesting and planting the backcross progeny seed to produce a backcross progeny plant, and (e) repeating steps (c) and (d) for at least three additional generations to produce a lettuce plant of variety 41-CR2360 RZ which can comprise at least one new trait and all of the physiological and morphological characteristics of a plant of lettuce variety 41-CR2360 RZ, when grown in the same environmental conditions. A lettuce plant produced by this method also forms part of the invention.

Mutations can be introduced randomly by means of one or more chemical compounds, such as ethyl methane sulphonate (EMS), nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast neutron exposure, X-rays, gamma irradiation, and/or by insertion of genetic elements, such as transposons, T-DNA, retroviral elements.

Mutations can also be introduced by more specific, targeted introduction of at least one modification by means of homologous recombination, oligonucleotide-based mutation introduction, zinc-finger nucleases (ZFN), transcription activator-like effector nucleases (TALENs) or Clustered Regularly Interspaced Short Palindromic Repeat (CRISPR) systems.

The invention further relates to a method of producing a plant of lettuce variety 41-CR2360 RZ which can comprise at least one new trait, the method which can comprise introducing a mutation or transgene conferring the at least one new trait into a plant of lettuce variety 41-CR2360 RZ, wherein a sample of seed of said variety has been deposited underNCIMB Accession No. 44249. A lettuce plant produced by this method also forms part of the invention.

In still a further embodiment, the invention provides a method of producing a lettuce seed which can comprise crossing a male parent lettuce plant with a female parent lettuce plant and harvesting the resultant lettuce seed, in which the male parent lettuce plant or the female parent lettuce plant is a lettuce plant of the invention, e.g. a lettuce plant having all of the morphological or physiological characteristics tabulated herein, including a lettuce plant of lettuce cultivar 41-CR2360 RZ, a sample of seed of which having been deposited under 44249. The resultant lettuce seed produced by this method and the lettuce plant that is produced by growing said lettuce seed also forms part of the invention.

In still a further embodiment, the invention provides a method of producing a lettuce cultivar which exhibits all of the physiological and morphological characteristics of lettuce variety 41-CR2360 RZ, a sample of seed of said variety having been deposited under NCIMB Accession No. 44249.

The invention even further relates to a method of producing lettuce leaves as a food product which can comprise: (a) sowing a seed of lettuce variety 41-CR2360 RZ, a sample of seed of which having been deposited under NCIMB Accession No. 44249, (b) growing said seed into a harvestable lettuce plant and (c) harvesting lettuce leaves or heads from the plant. The invention further comprehends packaging and/or processing the lettuce plants, heads or leaves.

Also encompassed by the invention is a container which can comprise one or more lettuce plants of the invention for harvest of leaves. The invention also comprehends a container having therein one or more heads of lettuce of the invention.

Further encompassed by the invention is a method of determining the genotype of a plant of lettuce variety 41-CR2360 RZ, a sample of seed of which has been deposited under NCIMB Accession No. 44249, or a first generation progeny thereof, which can comprise obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of lettuce variety 41-CR2360 RZ and/or give rise to the expression of any one or more, or all, of the physiological and morphological characteristics of lettuce variety 41-CR2360 RZ of the invention.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112(a)) or the EPO (Article 83 of the EPC), such that Applicants reserve the right and hereby disclose a disclaimer of any previously described product, process of making the product, or method of using the product. It can be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like (can have meaning attributed in U.S. Patent Law) (e.g. they can mean "includes", "included", "including", and that terms such as "consists essentially of" and "consisting essentially of" have the meaning ascribed to them in US Patent law, e.g., they allow for elements not explicitly recited, but exclude elements that are found in the prior art or that affect a basic or novel characteristic of the invention.

These and other embodiments are disclosed or are obvious from and encompassed by the following Detailed Description.

DEPOSITS

The Deposits with NCIMB Ltd, Wellheads Place, Dyce, Aberdeen AB21 7 GB, UK, on Oct. 20, 2023, under deposit accession number NCIMB 44249 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary, including if the deposit ever becomes unviable, during that period during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 2 depicts a detailed description of the development of lettuce variety 41-CR2360 RZ.

FIGS. 3A-3B depicts the characteristics of 41-CR2360 RZ.

DETAILED DESCRIPTION OF THE INVENTION

Figure 1:
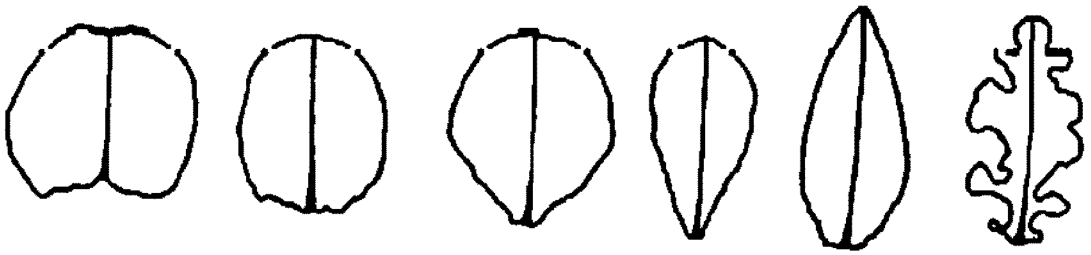
FIG. 1 depicts an illustration of six different shapes of the fourth leaf from a 20-day old seedling grown under optimal conditions.

The invention provides methods and compositions relating to plants, seeds and derivatives of a new lettuce variety herein referred to as lettuce variety 41-CR2360 RZ. Lettuce variety 41-CR2360 RZ is a uniform and stable line, distinct from other such lines.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., Principles of Cultivar Development, Volume I, MacMillan Publishing Co., which is hereby incorporated by reference.

When pedigree selection is applied, in general selection is first practiced among $F_2$ plants. In the next season, the most desirable F3 lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents can be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting can be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The $F_1$ can be self-pollinated to produce a segregating $F_2$ generation. Individual plants can then be selected which represent the desired phenotype in each generation ($F_3$, $F_4$, $F_5$, etc.) until the traits are homozygous or fixed within a breeding population.

A detailed description of the development of lettuce variety 41-CR2360 RZ is described in FIG. 2. The seedlot in year 7, seedlot 21R.1360, was deposited with the NCEVIB under deposit number 44249.

Breeding history of lettuce variety 41-CR2360 RZ (Pamelita RZ). Pedigree based line and plant selection, also known as pedigree selection, was used to develop the variety 41-CR2360 RZ (Pamelita RZ). Lettuce variety 41-CR2360 RZ (Pamelita RZ) is a pure line variety, derived from a single cross between Rijk Zwaan variety 41-342 RZ (Chicarita RZ) and internal Rijk Zwaan proprietary breeding line 102760, followed by 6 subsequent cycles of selection and selfing. After 1 generation, the variety 41-CR2360 RZ (Pamelita RZ) was established as uniform and stable. Parent line 41-342 RZ (Chicarita RZ) is publicly available and is homozygous. Parent line 102760 is not publicly available and is mostly homozygous.

In one embodiment, a plant of the invention has all the physiological and morphological characteristics of lettuce variety 41-CR2360 RZ. These characteristics of a lettuce plant of the invention, e.g. variety 41-CR2360 RZ, are summarized in FIGS. 3A-3B.

Next to the physiological and morphological characteristics mentioned in FIGS. 3A-3B, a plant of the invention also exhibits resistance to resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, and resistance to *Fusarium oxysporum* f. sp. *lactucae* race Fol:1.

As used herein resistance against *Bremia lactucae* is defined as the ability of a plant to resist infection by each of the various strains B1:29EU to B1:30EU, B1:32EU, BL:33EU and Bl:1US to Bl:9US of *Bremia lactucae* Regel. in all stages between the seedling stage and the harvestable plant stage. B1:29EU to B1:30EU, B1:32EU, BL:33EU means strains B1:29EU, B1:30EU, B1:32EU, B1:33EU (Van Ettekoven K, Van der Arend A J M, 1999. identification and denomination of 'new' races of *Bremia lactucae*. In: Lebeda A, Kristkova E (eds.) Eucarpia leafy vegetables '99. Palacky University, Olomouc, Czech Republic, 1999: 171-175; Van der Arend, A. J. M., Gautier, J., Guenard, M., Michel, H., Moreau, B., de Ruijter, J., Schut, J. W. and de Witte, I. (2003). Identification and denomination of 'new' races of *Bremia lactucae* in Europe by IBEB until 2002. In: Eucarpia leafy vegetables 2003. Proceedings of the Eucarpia Meeting on leafy vegetables genetics and breeding. Noordwijkerhout, The Netherlands. Eds. Van Hintum T., Lebeda A., Pink D., Schut J. pp 151-160; Van der Arend A J M, Gautier J, Grimault V, Kraan P, Van der Laan R, Mazet J, Michel H, Schut J W, Smilde D, De Witte I (2006) Identification and denomination of "new" races of *Bremia lactucae* in Europe by IBEB until 2006; incorporated herein by reference; Plantum NL (Dutch association for breeding, tissue culture, production and trade of seeds and young plants), IBEB press release, "New race of *Bremia lactucae* B1:27 identified and nominated", May 2010; Plantum NL, IBEB press release, "New races of *Bremia lactucae*, B1:29, B1:30 and B1:31 identified and nominated", August 2013; Plantum NL, IBEB press release, "A new race of *Bremia lactucae*, B1:32 identified and nominated in Europe", May 2015; Plantum NL, IBEB-EU press release, "A new race of *Bremia lactucae*, B1:33EU identified and denominated in Europe", May 2017; Plantum NL, IBEB-EU press release, "Two new races of *Bremia lactucae*, B1:34EU and B1:35EU identified and nominated in Europe", July 2018; Plantum NL, IBEB-EU press release, "A new race of *Bremia lactucae*, B1:36EU identified and denominated in Europe", July 2019; Plantum NL, IBEB EU press release, "A new race of *Bremia* lactuceae, B1:37EU identified and denominated in Europe, June 2021, IBEB-EU press release, "Denomination of New Official Downy Mildew Races in Lettuce", July 2023). Bl:1US to Bl:9US means Bl:1US, Bl:2US, Bl:3US, Bl:4US, Bl:5US, Bl:6US, Bl:7US, Bl:8US, Bl:9US (Schettini, T. M., Legg, E. J., Michelmore, R. W., 1991. Insensitivity to metalaxyl in California populations of *Bremia lactucae* and resistance of California lettuce cultivars to downy mildew, Phytopathology 81(1). p. 64-70; Michelmore R. & Ochoa. O. "Breeding Crisphead Lettuce." In: California Lettuce Research Board, Annual Report 2005-2006, 2006, Salinas, California, pp. 55-68).

Resistance typically is tested by two interchangeable methods, described by Bonnier, F. J. M. et al. (Euphytica, 61(3):203-211, 1992; incorporated herein by reference). One method involves inoculating 7-day old seedlings, and observing sporulation 10 to 14 days later. The other method involves inoculating leaf discs with a diameter of 18 mm obtained from a non-senescent, fully grown true leaf and observing sporulation 10 days later.

As used herein, resistance against *Nasonovia ribisnigri* (Mosley), or currant-lettuce aphid, is defined as the plant characteristic which results in a non-feeding response of the aphid on the leaves of the plant in all stages between 5 true-leaf stage and harvestable plant stage (U.S. Pat. No.

5,977,443 to Jansen, J. P. A., "Aphid Resistance in Composites," p. 12, 1999; incorporated herein by reference).

Resistance is tested by spreading at least ten aphids of biotype Nr:0 on a plant in a plant stage between 5 true leaves and harvestable stage, and observing the density of the aphid population on the plant as well as the growth reduction after 14 days in a greenhouse, with temperature settings of 23 degrees Celsius in daytime and 21 degrees Celsius at night. Day length is kept at 18 hours by assimilation lights.

As used herein, resistance against *Fusarium oxysporum* f. sp. *lactucae*, is defined as the ability of a plant to resist infection by race Fol:1. Resistance can be tested by two interchangeable methods. One method is described by Hubbard and Gerik (1993, Plant Disease 77(7): 750-754; incorporated herein by reference). The other test is described by Tsuchiya et al., (2004, J. Japan. Soc. Hort. Sci. 73(2): 105-113; incorporated herein by reference).

As used herein, crunchy lettuce is a new lettuce type, which has an oval head and leaf shape and very thick outer and inner leaves. The plant develops in an upright growing habit with thick, long and green, non-flabellate leaves. The younger leaves are longer than they are wide, cupping together to form an elongated loose head. Leaf margins are entire. Outer leaves range in color from light green to dark green. Inner heartleaves are smaller and range from light yellow to light green in color.

Embodiments of the inventions advantageously have one or more, and most advantageously all, of these characteristics.

In one aspect the invention provides a new type of lettuce (*Lactuca sativa*) variety, designated 41-CR2360 RZ. Lettuce cultivar 41-CR2360 RZ exhibits a combination of traits including resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head.

In an embodiment, the invention relates to lettuce plants that have all the physiological and morphological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that can be introduced by backcrossing, useful traits can be introduced directly into the plant of the invention, being a plant of lettuce variety 41-CR2360 RZ, by genetic transformation techniques; and, such plants of lettuce variety 41-CR2360 RZ that have additional genetic information introduced into the genome or that express additional traits by having the DNA coding there for introduced into the genome via transformation techniques, are within the ambit of the invention, as well as uses of such plants, and the making of such plants.

Genetic transformation can therefore be used to insert a selected transgene into the plant of the invention, being a plant of lettuce variety 41-CR2360 RZ or can, alternatively, be used for the preparation of transgenes which can be introduced by backcrossing. Methods for the transformation of plants, including lettuce, are well known to those of skill in the art.

Vectors used for the transformation of lettuce cells are not limited so long as the vector can express an inserted DNA in the cells. For example, vectors which can comprise promoters for constitutive gene expression in lettuce cells (e.g., cauliflower mosaic virus 35S promoter) and promoters inducible by exogenous stimuli can be used. Examples of suitable vectors include pBI binary vector. The "lettuce cell" into which the vector is to be introduced includes various forms of lettuce cells, such as cultured cell suspensions, protoplasts, leaf sections, and callus. A vector can be introduced into lettuce cells by known methods, such as the polyethylene glycol method, polycation method, electroporation, *Agrobacterium*-mediated transfer, particle bombardment and direct DNA uptake by protoplasts. To effect transformation by electroporation, one can employ either friable tissues, such as a suspension culture of cells or embryogenic callus or alternatively one can transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those which can be comprised of tungsten, platinum, and preferably, gold. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target lettuce cells. The screen disperses the particles so that they are not delivered to the recipient cells in large aggregates. It is believed that a screen intervening between the projectile apparatus and the cells to be bombarded reduces the size of projectiles aggregate and can contribute to a higher frequency of transformation by reducing the damage inflicted on the recipient cells by projectiles that are too large. Microprojectile bombardment techniques are widely applicable, and can be used to transform virtually any plant species, including a plant of lettuce variety 41-CR2360 RZ.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes can be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including lettuce plant cells, is well known in the art (See, e.g., U.S. Pat. Nos. 7,250,560 and 5,563,055).

Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for lettuce plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins (psaD, psaF, psaE, PC, FNR, atpC, atpD, cab, rbcS) (see U.S. Pat. No. 7,161,061), the CAB-1 promoter (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wunl, or (5) chemicals such as methyl jasmonate, salicylic acid, or Safener. It can also be advantageous to employ organ-specific promoters.

Exemplary nucleic acids which can be introduced to the lettuce variety of this invention include, for example, DNA sequences or genes from another species, or even genes or sequences which originate with or are present in lettuce species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene can already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of lettuce variety 41-CR2360 RZ. Non-limiting examples of particular genes and corresponding phenotypes one can choose to introduce into a lettuce plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. Patents that can concern transformed lettuce and/or methods of transforming lettuce or lettuce plant cells, and techniques from these U.S. Patents, as well as promoters, vectors, etc., can be employed in the practice of this invention to introduce exogenous nucleic acid sequence(s) into a plant of lettuce variety 41-CR2360 RZ (or cells thereof), and exemplify some exogenous nucleic acid sequence(s) which can be introduced into a plant of lettuce variety 41-CR2360 RZ (or cells thereof) of the invention, as well as techniques, promoters, vectors etc., to thereby obtain further plants of lettuce variety 41-CR2360 RZ, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material can comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which can comprise parts of the plant that are suitable for vegetative reproduction, for example cuttings, roots, stems, cells, protoplasts.

According to a further aspect thereof the propagation material of the invention can comprise a tissue culture of the claimed plant. The tissue culture can comprise regenerable cells. Such tissue culture can be derived from leaves, pollen, embryos, cotyledon, hypocotyls, meristematic cells, roots, root tips, anthers, flowers, seeds and stems. (See generally U.S. Pat. No. 7,041,876 on lettuce being recognized as a plant that can be regenerated from cultured cells or tissue).

Also, the invention comprehends methods for producing a seed of a "41-CR2360 RZ"-derived lettuce plant which can comprise (a) crossing a plant of lettuce variety 41-CR2360 RZ, a sample of seed of which having been deposited under NCIMB Accession No. 44249, with a second lettuce plant, and (b) whereby seed of a 41-CR2360 RZ-derived lettuce plant form. Such a method can further comprise (c) crossing a plant grown from 41-CR2360 RZ-derived lettuce seed with itself or with a second lettuce plant to yield additional 41-CR2360 RZ-derived lettuce seed, (d) growing the additional 41-CR2360 RZ-derived lettuce seed of step (c) to yield additional 41-CR2360 RZ-derived lettuce plants, and (e) repeating the crossing and growing of steps (c) and (d) for an additional 3-10 generations to further generate 41-CR2360 RZ-derived lettuce plants.

The invention further relates to the above methods that can further comprise selecting at steps b), d), and e), a 41-CR2360 RZ-derived lettuce plant, exhibiting one or more or all of the physiological and morphological characteristics of lettuce variety 41-CR2360 RZ, a sample of seed of said variety having been deposited under NCIMB Accession No. 44249, and other selected traits.

In particular, the invention relates to methods for producing a seed of a 41-CR2360 RZ-derived lettuce plant which can comprise (a) crossing a plant of lettuce variety 41-CR2360 RZ, a sample of seed of which having been deposited under NCEVIB Accession No. 44249, with a second lettuce plant and (b) whereby seed of a 41-CR2360 RZ-derived lettuce plant forms, wherein such a method can further comprise (c) crossing a plant grown from 41-CR2360 RZ-derived lettuce seed with itself or with a second lettuce plant to yield additional 41-CR2360 RZ-derived lettuce seed, (d) growing the additional 41-CR2360 RZ-derived lettuce seed of step (c) to yield additional 41-CR2360 RZ-derived lettuce plants and selecting plants exhibiting one or more or all of the physiological and morphological characteristics of lettuce variety 41-CR2360 RZ, and (e) repeating the crossing and growing of steps (c) and (d) for an additional 3-10 generations to further generate 41-CR2360 RZ-derived lettuce plants that exhibit one or more or all of the physiological and morphological characteristics of lettuce variety 41-CR2360 RZ.

The invention additionally provides a method of introducing at least one new trait into a plant of lettuce variety 41-CR2360 RZ which can comprise: (a) crossing a plant of lettuce variety 41-CR2360 RZ, a sample of seed of which having been deposited under NCEVIB Accession No. 44249, with a second lettuce plant that can comprise at least one new trait to produce progeny seed; (b) harvesting and planting the progeny seed to produce at least one progeny plant of a subsequent generation, wherein the progeny plant can comprise the at least one new trait; (c) crossing the selected progeny plant with a plant of lettuce variety 41-CR2360 RZ, to produce backcross progeny seed; (d) harvesting and planting the backcross progeny seed to produce a backcross progeny plant, (e) repeating steps (c) and (d) for at least three additional generations to produce backcross progeny that can comprise the at least one new trait and all of the physiological and morphological characteristics of a plant of lettuce variety 41-CR2360 RZ, when grown in the same environmental conditions. The invention, of course, includes a lettuce plant produced by this method.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. When a plant of lettuce variety 41-CR2360 RZ, a sample of seed of which having been deposited under NCIMB Accession No. 44249, is used in backcrossing, offspring retaining one or more or all of the physiological and morphological characteristics of lettuce variety 41-CR2360 RZ are progeny within the ambit of the invention. Backcrossing methods can be used with the present invention to improve or introduce a characteristic into a plant of the invention, being a plant of lettuce variety 41-CR2360 RZ. See, e.g., U.S. Pat. No. 7,705,206 (incorporated herein by reference consistent with the above INCORPORATION BY REFERENCE section), for a general discussion relating to backcrossing.

The invention further involves a method of determining the genotype of a plant of lettuce variety 41-CR2360 RZ, a sample of seed of which has been deposited under NCIMB Accession No. 44249, or a first generation progeny thereof, which can comprise obtaining a sample of nucleic acids from said plant and detecting in said nucleic acids a plurality of polymorphisms. This method can additionally comprise the step of storing the results of detecting the plurality of polymorphisms on a computer readable medium. The plurality of polymorphisms are indicative of and/or give rise to the expression of the physiological and morphological characteristics of lettuce variety 41-CR2360 RZ.

There are various ways of obtaining genotype data from a nucleic acid sample. Genotype data can be gathered which is specific for certain phenotypic traits (e.g. gene sequences), but also patterns of random genetic variation can be obtained to construct a so-called DNA fingerprint. Depending on the technique used a fingerprint can be obtained that is unique for lettuce variety 41-CR2360 RZ. Obtaining a unique DNA fingerprint depends on the genetic variation present in a variety and the sensitivity of the fingerprinting technique. A technique known in the art to provide a good fingerprint profile is called AFLP fingerprinting technique (See generally U.S. Pat. No. 5,874,215), but there are many other marker based techniques, such as RFLP (or Restriction fragment length polymorphism), SSLP (or Simple sequence length polymorphism), RAPD (or Random amplification of polymorphic DNA) VNTR (or Variable number tandem repeat), Microsatellite polymorphism, SSR (or Simple sequence repeat), STR (or Short tandem repeat), SFP (or Single feature polymorphism) DArT (or Diversity Arrays Technology), RAD markers (or Restriction site associated DNA markers) (e.g. Baird et al. PloS One Vol. 3 e3376, 2008; Semagn et al. African Journal of Biotechnology Vol. 5 number 25 pp. 2540-2568, 29 December, 2006). Nowadays, sequence-based methods are utilizing Single Nucleotide Polymorphisms (SNPs) that are randomly distributed across genomes, as a common tool for genotyping (e.g. Elshire et al. PloS One Vol. 6: e19379, 2011; Poland et al. PloS One Vol. 7: e32253; Truong et al. PLoS One Vol. 7 number 5: e37565, 2012).

With any of the aforementioned genotyping techniques, polymorphisms can be detected when the genotype and/or sequence of the plant of interest is compared to the genotype and/or sequence of one or more reference plants. As used herein, the genotype and/or sequence of a reference plant can be derived from, but is not limited to, any one of the following: parental lines, closely related plant varieties or species, complete genome sequence of a related plant variety or species, or the de novo assembled genome sequence of one or more related plant varieties or species. For example, it is possible to detect polymorphisms for the characteristic of resistance to downy mildew (*Bremia lactucae*) regarding specific Bl strains by comparing the genotype and/or the sequence of lettuce variety 41-CR2360 RZ with the genotype and/or the sequence of one or more reference plants. The reference plant(s) used for comparison in this example can for example be, but is not limited to, the comparison variety Chicarita RZ.

The polymorphism revealed by these techniques can be used to establish links between genotype and phenotype. The polymorphisms can thus be used to predict or identify certain phenotypic characteristics, individuals, or even species. The polymorphisms are generally called markers. It is common practice for the skilled artisan to apply molecular DNA techniques for generating polymorphisms and creating markers.

The polymorphisms of this invention can be provided in a variety of mediums to facilitate use, e.g. a database or computer readable medium, which can also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that can store computer searchable information.

As used herein, "computer readable media" refers to any medium that can be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan can readily appreciate how any of the presently known computer readable mediums can be used to create a manufacture which can comprise computer readable medium having recorded thereon a polymorphism of the present invention.

As used herein, "recorded" refers to the result of a process for storing information in a retrievable database or computer readable medium. For instance, a skilled artisan can readily adopt any of the presently known methods for recording information on computer readable medium to generate media which can comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats can be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan can readily appreciate that any one of the currently available computer-based system are suitable for use in the present invention.

Lettuce leaves are sold in packaged form, including without limitation as pre-packaged lettuce salad or as lettuce heads. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the lettuce leaves of the invention. Thus, the invention comprehends the use of and methods for making and using the leaves of the lettuce plant of the invention, as well as leaves of lettuce plants derived from the invention. The invention further relates to a container which can comprise one or more plants of the invention, or one or more lettuce plants derived from a plant of the invention, in a growth substrate for harvest of leaves from the plant in a domestic environment. This way the consumer can pick very fresh leaves for use in salads. More generally, the invention includes one or more plants of the invention or one or more plants derived from lettuce of the invention, wherein the plant is in a ready-to-harvest condition, including with the consumer picking his own, and further including a container which can comprise one or more of these plants.

The invention is further described by the following numbered paragraphs:

1. A seed of lettuce variety 41-CR2360 RZ, a sample of seed of said variety having been deposited under NCIMB Accession No. 44249.
2. A lettuce plant grown from the seed of paragraph 1.
3. A lettuce plant, or a part thereof, having all the physiological and morphological characteristics of the lettuce plant of paragraph 2.
4. A part of the lettuce plant of paragraph 2, wherein said part comprises a microspore, pollen, ovary, ovule, embryo sac, egg cell, cutting, root, stem, cell or protoplast.
5. A tissue culture of regenerable cells or protoplasts from the lettuce plant of paragraph 2.
6. A lettuce plant regenerated from the tissue culture of paragraph 5, wherein the regenerated plant expresses all of the physiological and morphological characteristics of lettuce variety 41-CR2360 RZ, a sample of seed of said variety having been deposited under NCEVIB Accession No. 44249.
7. A lettuce plant regenerated from the tissue culture of paragraph 5, wherein the regenerated plant is of lettuce variety 41-CR2360 RZ and exhibits a combination of traits or resistances including resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head, a sample of seed of said variety having been deposited under NCIMB Accession No. 44249.
8. A method of vegetatively propagating a plant of lettuce variety 41-CR2360 RZ, a sample of seed of said variety having been deposited under NCEVIB Accession No. 44249 comprising (a) collecting tissue capable of being propagated from the lettuce plant of paragraph 2, (b) cultivating the tissue to obtain proliferated shoots and rooting the proliferated shoots to obtain rooted plantlets, and (c) optionally growing plants from the rooted plantlets.
9. A method for producing a progeny plant of lettuce cultivar 41-CR2360 RZ, comprising crossing the lettuce plant of paragraph 2 with itself or with another lettuce plant, harvesting the resultant seed, and growing said seed.
10. A progeny plant produced by the method of paragraph 8, wherein said progeny exhibits all the morphological and physiological characteristics of the lettuce variety designated 41-CR2360 RZ, a sample of seed of said variety having been deposited under NCIMB Accession No. 44249.

11. A progeny plant produced by the method of paragraph 9, wherein said progeny is of lettuce variety 41-CR2360 RZ and exhibits a combination of traits or resistances including resistance to downy mildew (*Bremia lactucae*) races B1:29EU to B1:30EU, B1:32EU, BL:33EU and Bl:1US to Bl:9US, resistance to currant-lettuce aphid (*Nasonovia ribisnigri*) biotype Nr:0, resistance to *Fusarium oxysporum* f. sp. *lactucae* race Fol:1, a semi-erect leaf attitude and a dense head, a sample of seed of said variety having been deposited under NCEVIB Accession No. 44249.

12. The progeny plant of paragraph 10, wherein said progeny plant is modified in one or more other characteristics.

13. The progeny plant of paragraph 11, wherein the progeny plant is modified in one or more other characteristics.

14. The lettuce plant of paragraph 2 further comprising a transgene.

15. The plant of paragraph 14, wherein the transgene is introduced via transformation.

16. A method for producing a modified lettuce plant comprising mutagenizing the seed of paragraph 1 and growing said seed.

17. A method for producing a modified lettuce plant comprising mutagenizing the plant of paragraph 2.

18. A method for producing a modified lettuce plant comprising mutagenizing the plant of paragraph 3.

19. A method for producing a modified lettuce plant comprising mutagenizing the plant of paragraph 6.

20. A method for producing a modified lettuce plant comprising mutagenizing the plant of paragraph 7.

21. A method for producing a modified lettuce plant comprising mutagenizing the part of the plant of paragraph 4.

22. A method for producing a modified lettuce plant comprising mutagenizing the tissue culture of paragraph 5.

23. A method of producing a lettuce seed comprising crossing a male parent lettuce plant with a female parent lettuce plant and harvesting the resultant lettuce seed, wherein said male parent lettuce plant or said female parent lettuce plant is the lettuce plant of paragraph 2.

24. An F1 lettuce seed produced by the method of paragraph 23.

25. A lettuce plant produced by growing the seed of paragraph 24.

26. A method for producing a seed of a 41-CR2360 RZ-derived lettuce plant comprising (a) crossing a plant of lettuce variety 41-CR2360 RZ, a sample of seed of which having been deposited under NCIMB Accession No. 44249, with a second lettuce plant, and (b) whereby seed of a 41-CR2360 RZ-derived lettuce plant forms.

27. The method of paragraph 26 further comprising (c) crossing a plant grown from 41-CR2360 RZ-derived lettuce seed with itself or with a second lettuce plant to yield additional 41-CR2360 RZ-derived lettuce seed, (d) growing the additional 41-CR2360 RZ-derived lettuce seed of step (c) to yield additional 41-CR2360 RZ-derived lettuce plants, and (e) repeating the crossing and growing of steps (c) and (d) for an additional 3-10 generations to generate further 41-CR2360 RZ-derived lettuce plants, and (f) whereby seed of a 41-CR2360 RZ-derived lettuce plant forms.

28. A method of introducing at least one new trait into a plant of lettuce variety 41-CR2360 RZ comprising: (a) crossing the plant of paragraph 2, with a second lettuce plant that comprises at least one new trait to produce progeny seed, (b) harvesting and planting the progeny seed to produce at least one progeny plant of a subsequent generation, wherein the progeny plant comprises the at least one new trait, (c) crossing the progeny plant with a plant of lettuce variety 41-CR2360 RZ to produce backcross progeny seed, (d) harvesting and planting the backcross progeny seed to produce a backcross progeny plant, and (e) repeating steps (c) and (d) for at least three additional generations to produce a lettuce plant of variety 41-CR2360 RZ comprising at least one new trait and all of the physiological and morphological characteristics of a plant of lettuce variety 41-CR2360 RZ, when grown in the same environmental conditions.

29. The lettuce plant produced by the method of paragraph 24, wherein the plant comprises the at least one new trait and otherwise all of the physiological and morphological characteristics of a lettuce plant of lettuce variety 41-CR2360 RZ.

30. A method for producing lettuce leaves as a food product comprising sowing the seed of paragraph 1 and growing the seed into a harvestable lettuce plant and harvesting the head or leaves of said plant, optionally processing and/or packaging the head or the leaves.

31. A container comprising one or more lettuce plants of paragraph 2 for harvest of leaves.

32. The lettuce plant of paragraph 2, which is a plant grown from seed having been deposited under NCIMB Accession No. 44249.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A seed of lettuce variety 41-CR2360 RZ, a sample of seed of said variety having been deposited under NCIMB Accession No. 44249.

2. A lettuce plant grown from the seed of claim 1.

3. A lettuce plant, or a part thereof, having all the physiological and morphological characteristics of the lettuce plant of claim 2.

4. A part of the lettuce plant of claim 2, wherein said part comprises a microspore, pollen, ovary, ovule, embryo sac, egg cell, cutting, root, stem, cell or protoplast.

5. A tissue culture of regenerable cells or protoplasts from the lettuce plant of claim 2.

6. A lettuce plant regenerated from the tissue culture of claim 5, wherein the regenerated plant expresses all of the physiological and morphological characteristics of lettuce variety 41-CR2360 RZ, a sample of seed of said variety having been deposited under NCIMB Accession No. 44249.

7. A method of vegetatively propagating a plant of lettuce variety 41-CR2360 RZ, a sample of seed of said variety having been deposited under NCIMB Accession No. 44249, comprising (a) collecting tissue capable of being propagated from the lettuce plant of claim 2, (b) cultivating the tissue to obtain proliferated shoots and rooting the proliferated shoots to obtain rooted plantlets, and (c) optionally growing plants from the rooted plantlets.

8. A method for producing a progeny plant of lettuce cultivar 41-CR2360 RZ, comprising crossing the lettuce plant of claim 2 with itself or with another lettuce plant, harvesting the resultant seed, and growing said seed.

9. A progeny plant produced by the method of claim 7, wherein said progeny exhibits all the morphological and physiological characteristics of the lettuce variety designated 41-CR2360 RZ, a sample of seed of said variety having been deposited under NCIMB Accession No. 44249.

10. The lettuce plant of claim 2, wherein the plant expresses all of the physiological and morphological characteristics of lettuce variety 41-CR2360 RZ, a sample of seed of said variety having been deposited under NCIMB Accession No. 44249, further comprising a transgene.

11. The plant of claim 10, wherein the transgene is introduced via transformation.

12. A method for producing a modified lettuce plant comprising mutagenizing the seed of claim 1 and growing said seed.

13. A method for producing a modified lettuce plant comprising mutagenizing the plant of claim 2.

14. A method for producing a modified lettuce plant comprising mutagenizing the plant of claim 3.

15. A method for producing a modified lettuce plant comprising mutagenizing the plant of claim 6.

16. A method for producing a modified lettuce plant comprising mutagenizing the part of the plant of claim 4.

17. A method for producing a modified lettuce plant comprising mutagenizing the tissue culture of claim 5.

18. A method of producing a lettuce seed comprising crossing a male parent lettuce plant with a female parent lettuce plant and harvesting the resultant lettuce seed, wherein said male parent lettuce plant or said female parent lettuce plant is the lettuce plant of claim 2.

19. An F1 lettuce seed produced by the method of claim 18.

20. A lettuce plant produced by growing the seed of claim 19.

21. A method for producing a seed of a 41-CR2360 RZ-derived lettuce plant comprising (a) crossing a plant of lettuce variety 41-CR2360 RZ, a sample of seed of which having been deposited under NCIMB Accession No. 44249, with a second lettuce plant, and (b) whereby seed of a 41-CR2360 RZ-derived lettuce plant forms.

22. The method of claim 21 further comprising (c) crossing a plant grown from 41-CR2360 RZ-derived lettuce seed with itself or with a second lettuce plant to yield additional 41-CR2360 RZ-derived lettuce seed, (d) growing the additional 41-CR2360 RZ-derived lettuce seed of step (c) to yield additional 41-CR2360 RZ-derived lettuce plants, and (e) repeating the crossing and growing of steps (c) and (d) for an additional 3-10 generations to generate further 41-CR2360 RZ-derived lettuce plants, and (f) whereby seed of a 41-CR2360 RZ-derived lettuce plant forms.

23. A method of introducing at least one new trait into a plant of lettuce variety 41-CR2360 RZ comprising: (a) crossing the plant of claim 2, with a second lettuce plant that comprises at least one new trait to produce progeny seed, (b) harvesting and planting the progeny seed to produce at least one progeny plant of a subsequent generation, wherein the progeny plant comprises the at least one new trait, (c) crossing the progeny plant with a plant of lettuce variety 41-CR2360 RZ to produce backcross progeny seed, (d) harvesting and planting the backcross progeny seed to produce a backcross progeny plant, and (e) repeating steps (c) and (d) for at least three additional generations to produce a lettuce plant of variety 41-CR2360 RZ comprising at least one new trait and all of the physiological and morphological characteristics of a plant of lettuce variety 41-CR2360 RZ, when grown in the same environmental conditions.

24. The lettuce plant produced by the method of claim 19, wherein the plant comprises the at least one new trait and otherwise all of the physiological and morphological characteristics of a lettuce plant of lettuce variety 41-CR2360 RZ.

25. A method for producing lettuce leaves as a food product comprising sowing the seed of claim 1 and growing the seed into a harvestable lettuce plant and harvesting the head or leaves of said plant, optionally processing and/or packaging the head or the leaves.

26. A container comprising one or more lettuce plants of claim 2 for harvest of leaves.

* * * * *